United States Patent [19]

Breitbarth

[11] Patent Number: 5,502,056
[45] Date of Patent: Mar. 26, 1996

[54] CAFFEINE CONTAINING COMPOSITION

[76] Inventor: Richard Breitbarth, 10 Old Bloomfield Ave. P.O. Box 682, Pinebrook, N.J. 07058

[21] Appl. No.: 249,365

[22] Filed: May 27, 1994

[51] Int. Cl.⁶ .......................... A61K 31/52; A61K 7/00; A61K 33/44
[52] U.S. Cl. .......................... 514/263; 424/47; 424/125; 424/450; 424/489; 424/691; 424/724; 514/356; 514/567
[58] Field of Search .................... 424/724, 489, 424/691, 125, 450; 514/263, 356, 567

[56] References Cited

U.S. PATENT DOCUMENTS 4,443,546  4/1984  Stemerman et al. .................... 435/240
5,283,258  2/1994  Koch .................... 514/474

*Primary Examiner*—John W. Rollins
*Attorney, Agent, or Firm*—Evelyn M. Sommer

[57] ABSTRACT

A composition containing caffeine solubilized with para-amino benzoic acid is described. Preferably the caffeine is delivered in the form of an aqueous microdispersion including a non-metallic microparticulate carrier. Still more preferably, there is present in the aqueous microdispersion niacin. When administered orally, in small volumes, containing small doses of these agents, this composition has been demonstrated to have stimulant and antisoporific actions that result in elevated mood, decreased fatigue and increased capacity for work that is apparent almost immediately.

26 Claims, No Drawings

CAFFEINE CONTAINING COMPOSITION

This invention relates to a composition having stimulant and antisoporific activities. More particularly, this invention relates to a composition comprising caffeine solubilized with para-aminobenzoic acid (PABA). Still more particularly the compositions of the invention are provided in the form of aqueous microdispersions including a non-metallic microparticulate carrier for the solubilized caffeine. Further, this invention relates to a composition comprising caffeine solubilized with para-amino benzoic acid (PABA) and niacin, in the form of microdispersions including a non-metallic microparticulate carrier for the active agents having stimulant and antisoporific properties. The invention also provides a method of solubilizing caffeine and a method for treating subjects for overcoming fatigue, drowsiness, improving alertness, and imparting feelings of well being and enhanced energy.

BACKGROUND OF THE INVENTION

The compositions of the invention contain as active pharmacologic agents caffeine or caffeine solubilized with para-aminobenzoic acid, preferably in the form of aqueous microdispersions including a non-metallic microparticulate carrier for the caffeine. This composition, when administered orally, by spray pump, in a dosage of 2–6 drops (about 0.1–0.3 mls) contains about 12–17% caffeine. The composition of the invention preferably contains about 0.25–1.5% nicotinic acid. The resultant compositions have marked stimulant and antisoporific actions that result in elevated mood, decreased fatigue, increased capacity for work and more rapid and clearer flow of thoughts. The solubilization of the caffeine with the PABA permits the delivery of increased amounts of caffeine per unit dose. The microparticles act to extend the time the caffeine or caffeine and niacin remain active in the system and the niacin is effective in counteracting the effect of the caffeine on the blood vessels.

The amount of caffeine delivered of the herein described compositions in a 0.1 ml dose (about 2 drops) is about 14 mgs. One cup of coffer contains about 80–85 mgs of caffeine. The amount of caffeine provided in the compositions of the invention is therefore about ⅙th the amount of caffeine in a cup of coffee. The amount of niacin in 0.1 ml of a composition is about 0.5 mg. The conventional starting dose for niacin therapy is 100–200 mg TID and the maintenance dose is 0.65–2.0 rams TID. It should be apparent that the dosage of active agents as used in the instant compositions are very low.

The stimulating effects, antisoporific activity, mood elevation, decreased fatigue etc. are evident when the composition is formulated as an aqueous microdispersion of PABA solubilized caffeine, but even further advantages are realized when niacin is included.

The action of these two agents, solubilized caffeine and niacin, appears to be synergistic, i.e., their joint action or combined effect is greater than the algebraic sum of their individual effects. This synergistic action of caffeine has been noted previously, for example, caffeine is one of the best known "adjuvants" when used with pain relieving drugs such as aspirin or acetaminophen.

The compositions of the invention preferably contain in addition to the caffeine and niacin, when the latter is present an agent to increase the solubility of the caffeine. The solubility increasing component is para-aminobenzoic acid.

It has been found that this solubilizer is most effective and not only has enhanced solubilizing activity but there are no disadvantages associated with its use. A non-metallic microparticulate carrier for the PABA solubilized caffeine per se or in admixture with niacin is preferably included. The non-metallic microparticles (about 3–10 μm) can be silica, alumina, charcoal or other organic particles in appropriate form. The particles can also e present as liposomes. In addition saccharin in the form of its sodium salt, peppermint oil, licorice or vanilla extract can also be admixed into the compositions of the invention to make them more palatable. A surfactant, for example Tween 20 is also preferably included. The final volume is adjusted with water.

Caffeine is an alkaloid obtained from the leaves and seeds of the Coffera *arabica* or coffee plant and from the leaves of *Thea sinensis* or tea. Caffeine is a methylated xanthine having the formula $C_8H_{10}N_4O_2$, is anhydrous and has a molecular weight of 194.19. The solubility of methyl xanthine is low. In accordance with the invention a mixture of caffeine and PABA the latter for increasing the solubility of the caffeine (methyl xanthine) is preferred. Such mixture contains anhydrous caffeine and about equal amounts of solubilizer, (PABA) and is freely soluble in water and alcohol.

Although caffeine occurs naturally, it is prepared synthetically for commercial drug use. Both forms are equally suitable for use herein.

The known pharmacologic actions of caffeine include: (1) the relaxation of smooth muscle, notably bronchial muscle and the stimulation of voluntary skeletal muscle, increasing the force of contraction and decreasing associated muscular fatigue, (2) caffeine stimulates all levels of the central nervous system. In oral doses of 100–200 mg, the drug stimulates the cerebral cortex producing a more rapid and clearer though flow, wakefulness, or arousal in fatigued patients and improved psychomotor coordination as well as increased capability for sustained intellectual effort and decreased reaction time, and (3) action on the kidney to produce diuresis.

Caffeine is esentially non-toxic. The FDA has indicated that no fatal caffeine poisoning has ever been reported as the result of an overdose of this compound. The short term lethal dose of caffeine in adults is 5–10 grams. At moderate doses, caffeine poses little or no risk of developmental toxicity for the human fetus. These is no evidence that consumption of caffeine is causally related to the development of cancer or increased incidence of coronary heart disease.

Caffeine is readily absorbed after oral, rectal or parenteral administration. Maximal plasma concentrations are achieved within 1 hour. Caffeine has a half-life in plasma of 3–7 hours.

Caffeine is the only over-the-counter stimulant that meets the FDA standards for stimulants. The FDA has concurred that caffeine is both safe and effective. The recommended dose is 100–200 mg not to be administered more often than every 3 or 4 hours. The FDA has noted that, in contrast to the irritating qualities of many coffee extracts, caffeine itself, does not cause irritation of the gastro-intestinal tract in the usual doses. This is an advantage when the drug is used for its stimulant properties. The FDA, in its publications has stated that the evidence establishes that caffeine restores alertness when a person is drowsy or fatigued.

It has been estimated that the per capita intake of caffeine in the United States averages 170–200 mg/day. About 50% of this amount results from drinking coffee. One cup of coffee contains about 95 mg of caffeine, one cup of tea contains about 50 mg of caffeine, and cocoa contains about 5 mg per cup. A 12 oz (360 ml) bottle of cola contains 40–50 mg of caffeine, half of which has been added by the manufacturer.

Niacin the preferred additional active agent in the compositions of the invention occurs in two chemical forms, nicotinic acid and niacinamide and is a water soluble B vitamin having the formula $C_6H_5O_2N$ and a molecular weight of 123.1. Niacin and tryptophan (an amino acid that is converted to niacin in vivo) are found in yeast, liver, meat, fish, legumes, whole grains and enriched cereal products. Nicotinic acid functions in the body after conversion to either nicotinamide adenine dinucleotide (NAD) or nicotinamide adenine dinucleotide phosphate (NADP). NAD and NADP serve a vital role in metabolism as coenzymes for a wide variety of proteins that catalyze oxidation-reduction reactions essential for tissue respiration. It functions to maintain growth, maintain energy supply, maintain the respiratory cycle, maintain anabolism of hormones proteins and lipids. Nicotinic acid is readily absorbed from all portions of the intestine and the vitamin is distributed to all tissues. The niacin is used herein to counteract the effect of the caffeine on the circulatory system and namely its action as a vasoconstrictor.

The therapeutic or replacement dose of niacin is 100–1000 mg/day. There is no toxicity unless dosage exceeds 1–4 gms/kg. One third of a consumed total dose is excreted in 24 hours (half life). In daily doses of 1 gram or greater niacin decreases low density lipoproteins (LDL) and increases serum high density lipoproteins (HDL) in normal individuals or in those with hyperlipoproteinemia. Serum cholesterol and triglycerides are also decreased. The mechanism for this is unknown but is independent of the drug's role as a vitamin. Niacin in large doses produces peripheral vasodilation, the property taken advantage of herein. At usual doses, niacin-induced vasodilation is limited to cutaneous vessels.

Niacin is readily absorbed following oral administration, The amount needed for physiological function, as a vitamin, is (12–18 mg/day) Niacin is metabolized to nicotinamide which is widely distributed into body tissues. Nicotinamide is further metabolized in the liver and excreted in the urine.

PABA (para-aminobenzoic acid) is used in sun screens and has been shown to be very effective and also very safe. It is the standard against which all other sun screens are judged. It is widely used as a preservative. It has now been found by the inventor, herein to constitute a very effective solubilizer for caffeine.

The particulate matter suitable for use herein can be selected from a variety of differing materials including silica, alumina, charcoal and other organic particles. The particles are required to be of a size classified as microparticles and namely to have a particle diameter not exceeding 10 μm but preferably not exceeding 5 μm. Silica is a particularly preferred material. Silica particles are available in three main types: macroparticulate, microparticulate and pellicular. Macroparticular particles have a mean particle diameter larger than 40 μm and are not suitable for use herein; microparticulate particles have a mean particle diameter of between 3 and 10 μm, and have either a spherical or irregular shape. They have the highest efficiency and the greatest loading capacity because of the increase in surface area provided. Pellicular silica is characterized by having a thin pellicle or porous layer coated on solid micro-glass beads. The microparticulare silica particles are the preferred particles for uses herein. The microparticles, for example silica microparticles can be used directly. They are ionically charged, i.e., they carry a negative charge. The particles can be used directly or modified by first coating or chemically bonding an active phase onto the silica particle.

Liposomes are spherical particles in an aqueous medium formed by a lipid bilayer enclosing an aqueous compartment. Liposomes are formed by sonicating a lipid in an aqueous medium. They consist of spheres of lipid bilayers that enclose part of the aqueous medium. The liposome, "membrane", lipid bilayers allow for movement of active agents in and out of the sphere.

The pharmacologically active ingredients in the compositions of the invention, comprising caffeine solubilized by PABA or the latter solubilized caffeine and niacin, will be attached during the admixing of the components of the composition and microparticles to the charged ionic groups of the microparticles, directly or on to the modified or coated particles in such a manner that the active agents can readily and controllably be released for absorption through the mucous membrane of the oral cavity. Absorption through mucous membranes, unlike the skin, is rapid and has many advantages, and is therefore preferred in many instances as the route for administration of many medicaments, e.g., nitroglycerin, aspirin, antihistamines etc. The medicament enters the blood stream rapidly and by-passes the metabolism that occurs during oral ingestion. While not claimed herein, the use of the non-metallic microparticles as a carrier for such and other medicaments is proposed by the inventor herein.

The method for producing the basic composition takes place as follows:

The constituent ingredients for the composition of the invention, are continually stirred in a mixing vessel with a homogenizer (a high shear mixer (Greerco)). The constituent reagents are added to the water, under constant stirring in the mixing vessel. The first agent introduced into the water present in the mixing vessel is a preservative which can be any member of the group consisting of Sutacide A, in an amount between 0.3 and 0.5%, preferably 0.3% by volume; methylparaben in an amount between 0.5 and 2.0% but preferably 1.0% by volume; propylparaben in an amount between 0.1% and 0.2% but preferably 0.15% by volume; (the latter two can be used together); butylparaben; benzyl alcohol 0.9% by volume; sodium benzoate 0.1%, benzyl alkonium chloride etc. The ionically charged microparticles or liposomes (suspended in water) are added next in an amount between 4.0 and 4.1% but preferably 4.0% by volume. The preferred microparticles for use in the compositions of the invention are ionically charged silica particles, having a particle size of about 3 μm. The caffeine is then introduced into the vessel so that it will be present in an amount between 12 and 17% but preferably 14% by volume. The para-aminobenzoic acid for solubilizing agent is added in an amount between 12 and 17%, but preferably 14% by volume as the solublizer combines with the caffeine, molecule for molecule to form a salt. The solubilizers are added to the mixture while stirring is continued, as just noted to provide an amount wherein one molecule of solublizer will form a salt with one molecular of caffeine. If nicotinic acid is to be included, the nicotinic acid is then introduced and admixed using an amount of between 0.25 and 1.0% but preferably 0.5%. At this point, the pH of the admixture is adjusted to pH 7.03 with sodium hydroxide. A surfactant, such as Tween 20 is preferably included in an amount between 3.0 to 9.0% but preferably 4.0%. An agent for increasing the palability of the compositions such as sodium saccharinate, peppermint oil, vanilla extract, chocolate flavoring, licorice or the like can also be present, Any one member or more than one of these agents can be added next and is added as follows: sodium saccharinate in an amount between 0.25 to 1.0% but preferably 0.5%, peppermint oil in an amount between 0.35 to 0.75% but preferably 0.5%, vanilla extract in an amount between 0.1 to 0.5% but preferably 0.3%, or chocolate or licorice flavoring in an amount between 0.1 and 0.5% but preferably 0.3% by volume. Water is added to bring the total percentage to 100%.

The admixture may be dispensed for oral delivery in a number of ways: (1) atomizer (2) metered pump (3) squeeze bottle, or (4) bottle with a dropper having the prescribed amount of medication calibrated on the dropper. The container for application of the medication could be plastic, glass, stainless steel or treated metal. The atomizer or metered pump are preferable delivery systems. The atomizer yields a fine droplet spray or mist over a considerable oral area but the volume delivered is more difficult to control. The metered pump is used by first priming the pump, two depressions of the handle and then depressing the handle to deliver a given volume of fine spray or mist to the oral cavity (a given volume is dispensed with each depression of the handle).

The desired dose to be delivered by spray metered pump or atomizer is two to six drops. Each drop will contain 0.05 ml and the total dosage will be 0.1 to 0.3 ml or 14.0–42.0 mg of caffeine and 0.5–1.5 mg of niacin.

The following examples are provided for illustrating effective compositions in accordance with the invention:

EXAMPLE 1

| Agent | Amount (by volume) |
| --- | --- |
| parabens (methyl and propyl) | 0.2% |
| microparticles (silica) ionically charged suspended in water | 4.0% |
| caffeine | 15.0% |
| para-aminobenzoic acid | 15.0% |
| water to volume | about 62% |

EXAMPLE 2

| Agent | Amount (by volume) |
| --- | --- |
| parabens (methyl and propyl) | 0.2% |
| microparticles (silica) ionically charged, suspended in water | 4.0% |
| caffeine | 14.0% |
| para-aminobenzoic acid | 14.0% |
| nicotinic acid | 0.5% |
| Tween 20 | 4.0% |
| sodium saccharinate | 0.5% |
| peppermint oil | 0.5% |
| vanilla extract | 0.3% |
| water | to volume (about 60%) |

EXAMPLE 3

| Agent | Amount (by volume) |
| --- | --- |
| sodium benzoate | 0.1% |
| microparticles (silica) ionically charged, suspended in water | 4.0% |
| caffeine | 15.0% |
| para-aminobenzoic acid | 15.0% |
| niacin | 0.5% |
| water | to volume (about 65%) |

EXAMPLE 4

| Agent | Amount (by volume) |
| --- | --- |
| propylparaben | 0.15% |
| microparticles (alumina) ionically charged, suspended in water | 4.0% |
| caffeine | 14.0% |
| para-aminobenzoic acid | 14.0% |
| niacin | 0.5% |
| Tween 20 | 4.0% |
| licorice | 0.2% |
| water | to volume (about 63%) |

EXAMPLE 5

| Agent | Amount (by volume) |
| --- | --- |
| methylparaben | 0.5% |
| microparticles (silica) ionically charged, suspended in water | 4.0% |
| caffeine | 14.0% |
| para-aminobenzoic acid | 5.0% |
| nicotinic acid | 0.5% |
| Tween 20 | 4.0% |
| vanilla extract | 0.4% |
| water | to volume (about 73%) |

EXAMPLE 6

| Agent | Amount (by volume) |
| --- | --- |
| parabens (methyl and propyl) | 0.2% |
| microparticles, (silica) ionically charged, suspended in water | 4.0% |
| caffeine | 15.0% |
| para-aminobenzoic acid | 15.0% |
| niacin | 0.3% |
| Tween 20 | 5.0% |
| chocolate flavoring | 0.5% |
| sodium saccharinate | 0.5% |
| water | to volume (about 60%) |

EXAMPLE 7

| Agent | Amount |
| --- | --- |
| Sutacide A | 0.5% |
| microparticles,(silica) ionically charged, suspended in water | 4.0% |
| caffeine | 14.0% |
| para-aminobenzoic acid | 14.0% |
| peppermint oil | 0.5% |
| sodium saccharinate | 0.5% |
| water | to volume (about 66%) |

What is claimed is:

1. A composition having stimulant and antisoporific properties comprising caffeine solubilized with para-aminobenzoic acid affixed to non-metallic ionically charged microparticulate carrier particles in the form of a microdispersion in a pharmaceutically acceptable vehicle wherein said caffeine is present in an amount of 12–17%, said solubilizing agent is present in an amount of 12– 17% and said non-metallic ionically charged microparticulate carrier particles are present in an amount of 4–4.5%.

2. A composition according to claim 1 additionally containing niacin in an amount of 0.25–1.0%.

3. A composition according to claim 2 wherein said pharmaceutically acceptable vehicle is water.

4. A composition according to claim 3 which comprises

| | |
|---|---|
| solubilized caffeine | 12–17% |
| niacin | 0.25–1.0% |
| non-metallic microparticles | 4–4.5% |
| water | to 100% |

5. A composition according to claim 3 additionally containing at least one member selected from the group consisting of surfactants in an amount of 3.0–9.0%, preservatives in an amount of 0.1–2.5% and taste improving agents in an amount of 0.25–1.5%.

6. A composition according to claim 5 which comprises

| | |
|---|---|
| caffeine | 12–17% |
| niacin | 0.25–1% |
| non-metallic microparticles | 4–4.5% |
| preservative | 0.1–2.5% |
| caffeine solubilizer | 12–17% |
| surfactant | 3.0–9.0% |
| flavor improving agent | 0.25–1.5% |
| water | to 100% |

7. A composition according to claim 5 which comprises

| | |
|---|---|
| caffeine | 14.0% |
| niacin | 0.5% |
| non-metallic microparticles | 4.0% |
| preservative | 1.0% |
| caffeine solubilizer | 14.0% |
| surfactant | 4.0% |
| flavor improving agent | 0.5% |
| water | to 100% |

8. A composition according to claim 2 wherein said non-metallic microparticulate carrier particles have a particle size of about 3 to 10 μm.

9. A composition according to claim 2 wherein said non-metallic microparticulate carrier particles exhibit a negative charge.

10. A composition according to claim 2 wherein said non-metallic microparticulate carrier particles are selected from the group consisting of silica, alumina, charcoal and liposomes.

11. A composition according to claim 2 wherein said non-metallic microparticulate carrier particles are silica particles.

12. A composition according to claim 2 additionally containing a taste improvement agent in an amount of 0.25–1.5%.

13. A composition according to claim 12 wherein said taste improving agent is a member selected from the group consisting of saccharin, peppermint oil, licorice extract, chocolate flavoring and vanilla extract.

14. A composition according to claim 2 additionally containing a surfactant in an amount of 3.0–9.0%.

15. A composition according to claim 2 wherein said non-metallic microparticulate carrier particles have a particle diameter not exceeding 10 μm.

16. A composition according to claim 2 wherein said non-metallic microparticulate carrier particles have a particle diameter not exceeding 5 μm.

17. A composition according to claim 1 additionally containing water as said pharmaceutically acceptable vehicle and at least one member selected from the group consisting of surfactants in an amount of 3.0–9.0%, preservatives in an amount of 0.1– 2.5% and taste improving agents in an amount of 0.25–1.5%.

18. A composition according to claim 17 which comprises

| Agent | Amount (by volume) |
|---|---|
| [parabens (methyl and propyl)] methyl and propyl paraben | 0.2% |
| silica microparticles [silica] ionically charged suspended, in water | 4.0% |
| caffeine | 15.0% |
| para-aminobenzoic acid | 15.0% |
| water to volume | about 62% |

19. A method of preparing a composition according to claim 6 which comprises introducing into a mixing vessel containing water while maintaining the contents under constant stirring, in the sequence indicated said preservative, said non-metallic microparticles, said caffeine, reacting said caffeine with said solubilizing agent to form a salt in said mixing vessel, then introducing said niacin, adjusting the pH to 7.03 with sodium hydroxide, introducing said surfactant and then introducing the flavor improving agent whereby during said mixing said solubilized caffeine and niacin are attached to the charged groups of said non-metallic microparticles.

20. Method of treating a subject for allaying fatigue, drowsiness, and improved alertness, well being and energy level which comprises administering to such subject for absorption through a mucous membrane a therapeutically effective amount of a composition according to claim 2.

21. Method according to claim 20 which comprises administering said composition by means of a metered pump.

22. Method according to claim 20 which comprises administering said composition by means of a spray atomizer.

23. Method according to claim 20 wherein said composition is administered in drop wise fashion and each drop of said composition measures 0.05 ml.

24. Method according to claim 23 wherein the total dosage of composition administered is 2–6 drops containing 0.1 to 0.3 ml of said composition.

25. Method according to claim 24 wherein said 0.1–0.3 ml of composition contains 14.0–42 mg of caffeine and 0.5–1.5 mg of niacin.

26. Method of solubilizing caffeine which comprises reacting caffeine and para-aminobenzoic acid in equimolar amounts in an aqueous medium under thorough mixing to form a salt thereof.

* * * * *